(12) United States Patent
Lee

(10) Patent No.: US 6,203,319 B1
(45) Date of Patent: Mar. 20, 2001

(54) PELLET-FORMING MOLD FOR DENTAL FILLING MATERIALS

(76) Inventor: Edward Stanley Lee, 1237 Waterview Dr., Mill Valley, CA (US) 94941

( * ) Notice: Subject to any disclaimer, the term of this patent is extended or adjusted under 35 U.S.C. 154(b) by 0 days.

(21) Appl. No.: 09/452,561

(22) Filed: Dec. 1, 1999

(51) Int. Cl.[7] .................................................. A61C 19/00
(52) U.S. Cl. ............................ 433/34; 433/226; 249/54
(58) Field of Search ......................... 433/34, 36, 226; 249/53, 119; 264/16; 425/DIG. 11, 576

(56) References Cited

U.S. PATENT DOCUMENTS

| | | | |
|---|---|---|---|
| 170,975 | * 12/1875 | Wetmore | 249/119 |
| 3,638,314 | 2/1972 | Lopez | 433/83 |
| 5,125,842 | * 6/1992 | Hiltunen | 433/226 |
| 5,368,481 | * 11/1994 | Hill | 433/159 |

* cited by examiner

Primary Examiner—John J. Wilson
Assistant Examiner—Melba Bumgarner

(57) ABSTRACT

A mold used to form small pellets of dental filling material. The mold has several flat surfaces, on which several individual pellet-forming grooves (12a–d) are located. A handle is attached to one end (10).

1 Claim, 2 Drawing Sheets

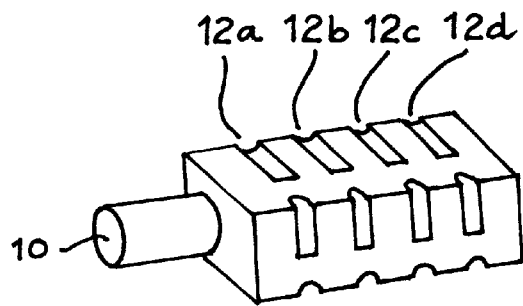
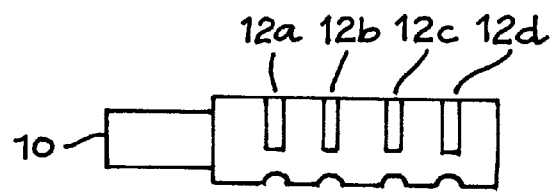
FIG. 1      FIG. 2
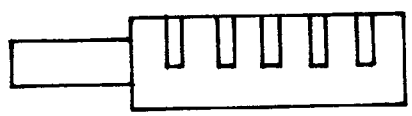
FIG. 3      FIG. 4

PELLET-FORMING MOLD FOR DENTAL FILLING MATERIALS

BACKGROUND

1. Field of Invention

This invention relates to a dental filling device, specifically to a device used to form and shape small pellets of dental filling material prior to placement in a tooth cavity preparation.

2. Description of Prior Art

Certain kinds of tooth cavity preparations can be very small. Presently, the tool used to deliver a dental filling material to these small cavity preparations is an amalgam carrier. U.S. Pat. No. 3,638,314 to Lopez and Valdes describes such a device. This device works by first loading a hollow, cylindrical tube at one end with a filling material. The plunger is located on the opposite end. The plunger is pushed to express the loaded filling material from the carrier into a cavity preparation.

The amalgam carrier suffers from a number of disadvantages:

(a) The small cavity preparation is usually much smaller than the barrel of the amalgam carrier. Filling the small cavity preparation with this device will result in a gross amount of material outside, not into, the cavity preparation. The filling process with the amalgam carrier is difficult, laborious and messy.

(b) The bulky amalgam carrier is useless when the filling is done in a difficult to reach location of the mouth.

(c) The amalgam carrier is unable to control the amount of filling material and can be used only with amalgam.

(d) The amalgam carrier is costly.

BRIEF SUMMARY OF THE INVENTION

Several objects and advantages of the present invention are:

a) to provide a new and simple way of delivering a dental filling material to a small cavity preparation.

b) to form and deliver manageable amounts of a dental filling material to a small cavity preparation.

c) to provide an expeditious way of delivering a dental filling material.

d) to provide a device that can be used with a variety of dental filling materials.

Further objects and advantages of my invention will become apparent from a consideration of the drawings and ensuing descriptions.

DRAWING FIGURES

FIG. 1 shows various aspects of the mold with the cylindrical handle on one end and grooves in the rectangular flat surfaces.

FIG. 2 shows a top view of the mold with grooves in the rectangular surface and the cylindrical handle extending from the side of the rectangular block.

FIGS. 3 and 4—alternative embodiments. FIG. 3 shows five grooves in the rectangular flat surface. FIG. 4 shows one longer groove extending towards the shorter edge of the rectangular flat surface.

Figure 5:
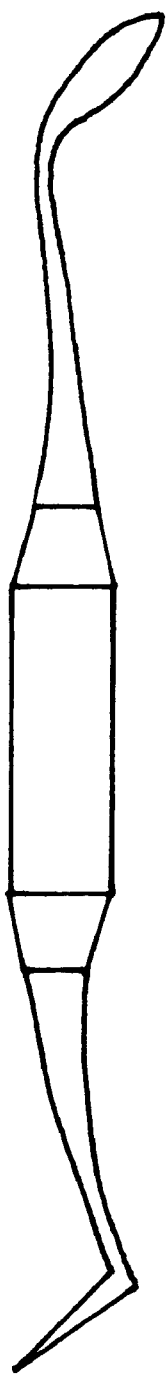
Figure 6:
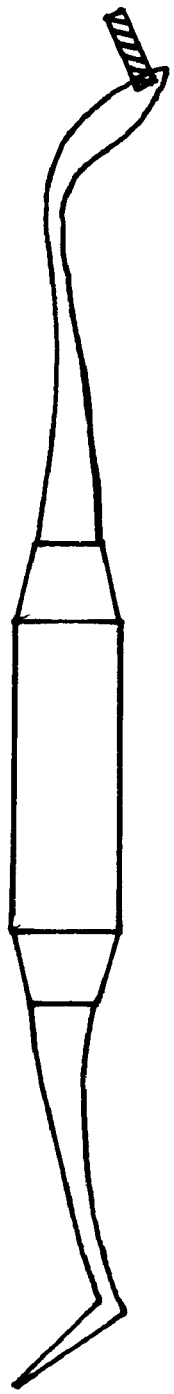

FIGS. 5 and 6—other illustrations. FIG. 5 shows an overview of the #3 Hollenback dental instrument, (G. Hartzell & Sons, Walnut Creek, Calif.). FIG. 6 shows a pellet of dental filling at the tip of the #3 Hollenback instrument.

DETAILED DESCRIPTION OF THE INVENTION

FIG. 1 shows an overall view of the basic version of my pellet-forming mold. The mold is made of plastic or any other material which has a smooth surface.

The rectangular block section is 1 cm in height, 1 cm in width, and 4 cm in length. Handle 10 is cylindrical, measuring 2 cm in length and 0.75 cm in diameter. Handle 10 is attached to the rectangular block by an adhesive or fusion of any means.

Four longitudinal grooves 12 a–d are placed on all four surfaces of the mold. The grooves are extending from the inside of the rectangular surface towards the outer edge. The grooves are formed by a machining process. The grooves vary in depth from 2 to 4 mm.

FIG. 3 shows five grooves in the rectangular flat surface. FIG. 4 shows one longer groove extending toward the shorter edge of the rectangular flat surface.

A dental-filling material is mixed according to the manufacture directions. The filling material is brought to the pellet-forming mold and placed into the grooves using a dental spatula. A #3 Hollenback dental instrument (FIG. 5) is used to scoop the filling material out of the groove. The filling materials have an adhesive quality, so what results is a nicely formed, perpendicular pellet of filling material resting at the tip of the Hollenback instrument (FIG. 6). The filling material is then inserted into the cavity preparation and condensed into place using a dental plugger instrument.

Accordingly, the reader will see that the pellet forming mold offers a number of advantages: ease of use through simplicity in design, delivery of a controlled and manageable amount of filling material in an efficient manner, economical to manufacture and versatility of use with a variety of dental filling materials.

While my above description contains many specifications, these should not be construed as limitations on the scope of the invention, but rather a preferred embodiment thereof. Many other variations are possible. For example, the mold could be made from various types of plastics, metals, ceramics or glass. The mold could be made different colors to contrast itself from the filling material. The length, depth and number of grooves within the mold can vary. The mold shape and number of surfaces can also vary.

Accordingly, the scope of the invention should be determined not by the embodiments illustrated, but by it's claim and the legal equivalents.

I claim:

1. A molding device used to form pellets from any kind of dental filling material for delivery into a tooth cavity preparation, comprising:

a) a polygon having 3 or more sides, each side defining a surface, b) a plurality of grooves on each surface for receiving a dental filling material, c) grooves varying in length between 1 to 6 mm, width between 0.5 to 2 mm and depth between 0.5 to 2 mm, and d) an attached handle.

* * * * *